US010617611B2

(12) United States Patent
Takei et al.

(10) Patent No.: US 10,617,611 B2
(45) Date of Patent: Apr. 14, 2020

(54) CORE-SHELL TYPE POLYMER PARTICLE, AQUEOUS POLYMER EMULSION, AND HAIR COSMETIC COMPOSITION

(71) Applicant: Mitsubishi Chemical Corporation, Chiyoda-ku (JP)

(72) Inventors: Kiyomi Takei, Mie (JP); Akira Ishikubo, Mie (JP); Yuji Soejima, Mie (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/553,415

(22) Filed: Aug. 28, 2019

(65) Prior Publication Data

US 2019/0380926 A1      Dec. 19, 2019

Related U.S. Application Data

(63) Continuation of application No. 15/615,047, filed on Jun. 6, 2017, which is a continuation of application No. PCT/JP2015/084385, filed on Dec. 8, 2015.

(30) Foreign Application Priority Data

Dec. 8, 2014   (JP) ................................ 2014-247738

(51) Int. Cl.
| | | |
|---|---|---|
| *A61K 8/06* | (2006.01) | |
| *A61Q 5/12* | (2006.01) | |
| *A61Q 5/06* | (2006.01) | |
| *A61Q 5/02* | (2006.01) | |
| *A61K 8/898* | (2006.01) | |
| *A61K 8/81* | (2006.01) | |
| *A61K 8/31* | (2006.01) | |
| *A61K 8/19* | (2006.01) | |
| *A61K 8/891* | (2006.01) | |

(52) U.S. Cl.
CPC ................. *A61K 8/06* (2013.01); *A61K 8/19* (2013.01); *A61K 8/31* (2013.01); *A61K 8/81* (2013.01); *A61K 8/8152* (2013.01); *A61K 8/891* (2013.01); *A61K 8/898* (2013.01); *A61Q 5/02* (2013.01); *A61Q 5/06* (2013.01); *A61Q 5/12* (2013.01); A61K 2800/54 (2013.01)

(58) Field of Classification Search
CPC . A61K 8/06; A61K 8/81; A61K 8/898; A61K 8/19; A61K 8/8152; A61K 8/891; A61K 8/31; A61K 2800/54; A61Q 5/02; A61Q 5/06; A61Q 5/08; A61Q 5/12
See application file for complete search history.

(56) References Cited

U.S. PATENT DOCUMENTS

| | | |
|---|---|---|
| 3,927,199 A | 12/1975 | Micchelli et al. |
| 4,358,567 A | 11/1982 | Hayama et al. |
| 4,921,915 A | 5/1990 | Dengler et al. |
| 5,476,660 A | 12/1995 | Somasundaran et al. |
| 5,643,672 A | 7/1997 | Marchi et al. |
| 6,113,890 A | 9/2000 | Young et al. |
| 6,375,932 B1 | 4/2002 | Hiwatashi et al. |
| 7,008,751 B2 | 3/2006 | Tao et al. |
| 2005/0042189 A1 | 2/2005 | Balliello |
| 2005/0112152 A1 | 5/2005 | Popplewell et al. |
| 2005/0153135 A1 | 7/2005 | Popplewell et al. |
| 2006/0024255 A1 | 2/2006 | Quadir et al. |
| 2007/0015669 A1 | 1/2007 | Zhang |
| 2009/0053160 A1 | 2/2009 | Khoshdel et al. |
| 2010/0197526 A1 | 8/2010 | Zhang |
| 2010/0316850 A1 | 12/2010 | Tao et al. |
| 2012/0259021 A1 | 10/2012 | Jiang et al. |
| 2014/0221577 A1 | 8/2014 | Jiang et al. |
| 2017/0292061 A1 | 10/2017 | Zhang |
| 2017/0292065 A1 | 10/2017 | Zhang |

FOREIGN PATENT DOCUMENTS

| | | |
|---|---|---|
| CN | 1176094 A | 3/1998 |
| CN | 1200023 A | 11/1998 |
| CN | 101171306 A | 4/2008 |
| CN | 102804067 | * 11/2012 |
| CN | 102804067 A | 11/2012 |
| CN | 102906127 A | 1/2013 |
| EP | 0 253 254 A2 | 1/1988 |
| EP | 025324244 | * 1/1988 |
| EP | 1 627 664 A1 | 2/2006 |
| EP | 2440977 | * 4/2012 |
| EP | 2440977 | 4/2012 |
| FR | 2 695 558 A1 | 3/1994 |
| FR | 2 994 839 A1 | 3/2014 |
| JP | 49-14647 | 2/1974 |
| JP | 51-9732 | 1/1976 |
| JP | 55-104209 | 8/1980 |
| JP | 63-39909 | 2/1988 |
| JP | 2007-1969 | 1/2007 |

(Continued)

OTHER PUBLICATIONS

Christodoulakis et al, "Amphoteric Core Shell Microgel Colloidal Particles", vol. 26, No. 2m, pp. 639-647 (Year: 2010).*
International Search Report dated Mar. 8, 2016 in PCT/JP2015/084385 filed Dec. 8, 2015 (with English translation).
Written Opinion dated Mar. 8, 2016 in PCT/JP2015/084385 filed Dec. 8, 2015.
Extended European Search Report dated Dec. 15, 2017 in European Patent Application No. 15867962.1 10 pages.
Kostas E. Christodoulakis, et al. "Amphoteric Core-Shell Microgels: Contraphilic Two-Compartment Colloidal Particles", Langmuir, XP-002775559, vol. 26, No. 2, Jan. 19, 2010, pp. 639-647.

(Continued)

*Primary Examiner* — Carlos A Azpuru
(74) *Attorney, Agent, or Firm* — Oblon, McClelland, Maier & Neustadt, L.L.P.

(57) ABSTRACT

The present invention relates to a core-shell type polymer particle including a shell part composed of an amphoteric polymer (A) and a core part composed of a hydrophobic polymer (B).

10 Claims, No Drawings

(56) References Cited

FOREIGN PATENT DOCUMENTS

| | | |
|---|---|---|
| JP | 2008-540365 | 11/2008 |
| JP | 2011-219367 | 11/2011 |
| JP | 2012-529669 | 11/2012 |
| JP | 2012-529669 A1 | 11/2012 |
| JP | 2013-510229 | 3/2013 |
| JP | 2013-245313 A | 12/2013 |
| WO | WO 03/037991 A1 | 5/2003 |
| WO | WO 2006/116868 A1 | 11/2006 |
| WO | WO 2007/146680 A1 | 12/2007 |
| WO | WO 2010/144119 A1 | 12/2010 |
| WO | WO 2014/037306 A1 | 3/2014 |

OTHER PUBLICATIONS

Office Action dated Mar. 12, 2019, in Chinese Patent Application No. 201580066537.0 (w/ English translation).
Office Action dated Mar. 20, 2019, in EP Patent Application No. 15 867 962.1.
Japanese Office Action dated Jun. 25, 2019, in Patent Application No. 2015-238975, 18 pages (with unedited computer generated English translation).
Office Action dated Nov. 20, 2019, in Chinese Patent Application No. 201580066537.0 (w/ Computer-generated English translation).
Office Action dated Jan. 29, 2020 in European Patent Application No. 15867962.1.

* cited by examiner

CORE-SHELL TYPE POLYMER PARTICLE, AQUEOUS POLYMER EMULSION, AND HAIR COSMETIC COMPOSITION

CROSS-REFERENCE TO RELATED APPLICATIONS

The present application is a continuation application of U.S. patent application Ser. No. 15/615,047, filed Jun. 6, 2017, which in turn is a continuation application of International Application No. PCT/JP2015/084385, filed Dec. 8, 2015, which claims priority to Japanese Patent Application No. 2014-247738, filed Dec. 8, 2014. The contents of these applications are incorporated herein by reference in their entirety.

TECHNICAL FIELD

The present invention relates to a core-shell type polymer particle which is, for example, used as an emulsion for cosmetics, an aqueous polymer emulsion having the core-shell type polymer particle dispersed in water, and a hair cosmetic composition including the polymer emulsion blended therein.

BACKGROUND ART

It is well known that the hair is fixed with a resin to give a desired shape. As such a resin for cosmetics, various ionic polymers inclusive of anionic polymers, for example, acrylic, vinyl acetate-based, vinylpyrrolidone-based, or vinyl methyl ether-based polymers, are generally known. Films formed of such a resin are usually hard and brittle, so that they are insufficient in flexibility and involve such an aspect that a finish feeling of the hair is stiff, and a natural texture is failed.

In particular, when it was intended to enhance a hairdressing effect, the results that the film becomes harder, thereby more deteriorating the finish feeling of the hair were brought. In addition, cationic acrylic polymers, vinylpyrrolidone-based polymers, or vinyl methyl ether-based polymers become very flexible at the time of high temperature and high humidity, thereby easily causing a sticky phenomenon, and also the hairdressing effect tends to be lowered. In addition, because of poor slippage of the film, a touch feeling of the hair was also not good.

As for materials capable of improving these defects of resins, amphoteric macromolecular polymers having flexibility of film are described in Patent Literatures 1 to 3. Furthermore, as for materials capable of more improving the slippage of films, a hair cosmetic containing an acrylic-urethane emulsion described in Patent Literature 4 is known.

BACKGROUND ART LITERATURE

Patent Literature

Patent Literature 1: JP-A-S49-14647
Patent Literature 2: JP-A-S51-9732
Patent Literature 3: JP-A-S55-104209
Patent Literature 4: JP-A-2007-001969

SUMMARY OF INVENTION

Technical Problem

However, when the polymers or emulsion described in the above-described literatures are used for a hair cosmetic, although the flexibility can be improved, there is such a problem that a setting power or humidity resistance is lowered. In addition, although many of conventional polymers used for a hairdressing agent or the like are usually sufficient in the hardness and setting power, the softness of the touch feeling is therefore sacrificed, and there is such a problem that the compatibility between hardness and softness is insufficient. Accordingly, the development of, as a polymer to be used for a hairdressing agent or the like, a resin having not only flexibility, suppleness, and softness but also humidity resistance and a setting power is demanded.

An object of the present invention is to solve the above-described problems and to provide a core-shell type polymer particle not only having hardness, softness, and humidity resistance but also being capable of forming a film which is easily washed and removed, an aqueous polymer emulsion, and a hair cosmetic composition.

Solution to Problem

In order to achieve the above-described object, the inventors of the present invention made extensive and intensive investigations. As a result, it has been found that a specified core-shell type polymer particle composed of an amphoteric polymer and a hydrophobic polymer not only has hardness, suppleness, softness, and humidity resistance but also makes it possible to form a film that is easily washed and removed, leading to the present invention. Specifically, the gist of the present invention resides in the following [1] to [10].

[1] A core-shell type polymer particle comprising a shell part composed of an amphoteric ion polymer (A) and a core part composed of a hydrophobic polymer (B).

[2] The core-shell type polymer particle according to [1], wherein the amphoteric polymer (A) contains a repeating unit derived from an unsaturated monomer having a betaine structural group.

[3] The core-shell type polymer particle according to [1], wherein the amphoteric polymer (A) contains a repeating unit derived from an unsaturated monomer having an amine oxide group.

[4] The core-shell type polymer particle according to [1], wherein the amphoteric polymer (A) contains a repeating unit derived from an unsaturated monomer having an anion group selected from the group consisting of a carboxyl group, a sulfonic acid group, and a phosphoric acid group, and further contains at least one of a repeating unit derived from an unsaturated monomer having a tertiary amino group and a repeating unit derived from an unsaturated monomer having a quaternary ammonium group.

[5] The core-shell type polymer particle according to any one of [1] to [4], wherein a mass ratio of the amphoteric polymer (A) to the hydrophobic polymer (B) [(A)/(B)] is 1/10 to 10/1

[6] The core-shell type polymer particle according to any one of [1] to [5], wherein a glass transition temperature of the hydrophobic polymer (B) is $-70°$ C. or higher and $105°$ C. or lower.

[7] The core-shell type polymer particle according to any one of [1] to [6], wherein the hydrophobic polymer (B) contains a structural unit derived from a hydrophobic unsaturated monomer (b), and the hydrophobic unsaturated monomer (b) contains an alkyl (meth)acrylate having a hydrocarbon chain having 1 to 45 carbon atoms.

[8] An aqueous polymer emulsion comprising the core-shell type polymer particle according to any one of [1] to [7] dispersed in water.

[9] The aqueous polymer emulsion according to [8], wherein an average particle diameter of the core-shell type polymer particle dispersed in the aqueous polymer emulsion is 10 nm to 10 μm.

[10] A hair cosmetic composition comprising the aqueous polymer emulsion according to [8] or [9] blended therein.

Effect of the Invention

The core-shell type polymer particle, the aqueous polymer emulsion, and the hair cosmetic composition of the present invention sufficiently secure water solubility of an emulsion, also have hardness, suppleness, and humidity resistance, and are capable of forming a film which is easily washed and removed. In particular, the core-shell type polymer particle and the aqueous polymer emulsion of the present invention are excellent in adhesion to the hair and capable of giving favorable setting effect and texture, and therefore, they are especially suitable as a hair cosmetic, such as hair spray, mousse, setting lotion, gel, spray, etc.

DESCRIPTION OF EMBODIMENTS

<Shell Part in Core-Shell Type Polymer Particle>

The shell part in the core-shell type polymer particle of the present invention is composed of an amphoteric polymer (A) having both a cation and an anion within the polymer. In view of the fact that the polymer has an anion therein, a setting power and a holding power can be revealed. In addition, in view of the fact that the polymer has a cation therein, an affinity with the hair can be improved.

In view of the fact that the amphoteric polymer (A) in the core-shell type polymer particle of the present invention has both a cation and an anion within the polymer, it is possible to make the affinity with the hair favorable with sufficiently having a setting power and a holding power.

In view of the fact that the core-shell type polymer particle of the present invention has the amphoteric polymer (A) in the shell part, the characteristics of the amphoteric polymer (A) can be exhibited directly against the hair.

Examples of the amphoteric polymer (A) include polymers composed of, as an essential component, an unsaturated monomer containing a betaine structural group, such as a carboxybetaine group, a sulfobetaine group and a phosphobetaine group; polymers composed of, as an essential component, an unsaturated monomer having an amine oxide group; polymers composed of, as essential components, an unsaturated monomer having an anion group, such as a carboxyl group, a sulfonic acid group and a phosphoric acid group, and at least one of an unsaturated monomer having a group having a quaternary ammonium salt (hereinafter also referred to as a quaternary ammonium group) and an unsaturated monomer having a tertiary amino group; and the like.

Specific examples of the polymer composed of, as an essential component, an unsaturated monomer having a betaine structural group include methacrylic carboxybetaine polymers that are a monohaloacetate-modified product of a dimethylaminoethyl methacrylate/alkyl methacrylate copolymer, such as YUKAFORMER 205S, YUKAFORMER SM, AMPHOSET, YUKAFORMER 301, YUKAFORMER 104D, YUKAFORMER 202, YUKAFORMER 510, YUKAFORMER FH, YUKAFORMER 204WL, and YUKAFORMER 204WL-2 (all of which are manufactured by Mitsubishi Chemical Corporation).; and the like. These polymers are disclosed in, for example, JP-A-S51-9732, JP-A-S55-104209, JP-A-S61-258804, JP-A-7-285832, and the like.

The polymer composed of, as an essential component, an unsaturated monomer having an amine oxide group (resin containing amine oxide group) is a polymer having, as a constituent component, a fatty acid acrylate having 1 to 24 carbon atoms, an ethylamine oxide methacrylate, and at least one of acrylic acid and methacrylic acid and contains an amine oxide group as a structural unit. Specific examples thereof include DIAFORMER Z-711, DIAFORMER Z-712, DIAFORMER Z-631, DIAFORMER Z-632, DIAFORMER Z-732, DIAFORMER Z-651, DIAFORMER Z-731, and DIAFORMER Z-772 (all of which are manufactured by Mitsubishi Chemical Corporation), and the like.

Specific examples of the polymer composed of, as essential components, an unsaturated monomer having an anion group, such as a carboxyl group, a sulfonic acid group and a phosphoric acid group, and at least one of an unsaturated monomer having a quaternary ammonium group and an unsaturated monomer having a tertiary amino group include polymers composed of, as essential components, an unsaturated monomer having a carboxyl group and an unsaturated monomer having a tertiary amino group, that is a hydroxypropyl acrylate/butylaminoethyl methacrylate/octylamide acrylate copolymer, such as UNFOAMER 28-4910, UNFOAMER LV-71, and UNFOAMER LV-47 (all of which are manufactured by Akzo Nobel N.V.).; polymers composed of, as essential components, an unsaturated monomer having a carboxyl group and an unsaturated monomer having a quaternary ammonium group, that is a diallyldimethylammonium chloride/acrylic acid copolymer, such as MERQUAT 295 (manufactured by Lubrizol Corporation), or a diallyldimethylammonium chloride/acrylic acid/acrylamide copolymer, such as MERQUAT PLUS 3330 (manufactured by Lubrizol Corporation); and the like.

From the viewpoint of improving the affinity with the hair, thereby enabling the hairdressing effect to be improved especially at high temperature and high humidity, it is preferred that the amphoteric polymer (A) contains a repeating unit derived from an unsaturated monomer having a betaine structural group.

In addition, from the viewpoint of not only improving the affinity with the hair but also enabling the stimulativeness to the skin to be more lowered, it is preferred that the amphoteric polymer (A) contains a repeating unit derived from an unsaturated monomer having an amine oxide group.

In addition, from the viewpoints that a natural finish can be achieved without causing stickiness, and the moisture retention can be improved, it is preferred that the amphoteric polymer (A) contains a repeating unit derived from an unsaturated monomer having an anion group selected from the group consisting of a carboxyl group, a sulfonic acid group, and a phosphoric acid group and at least one of a repeating unit derived from an unsaturated monomer having a quaternary ammonium group and a repeating unit derived from an unsaturated monomer having a tertiary amino group.

<Core Part in Core-Shell Type Polymer Particle>

The core part in the core-shell type polymer particle of the present invention is composed of a hydrophobic polymer (B). It is preferred that a glass transition temperature of the hydrophobic polymer (B) is −70° C. or higher and 105° C. or lower. In this case, the film formability can be improved. Furthermore, in this case, the suppleness of the film can be improved, and the generation of flaking can be more prevented from occurring. From the viewpoint of improving the strength of the film, the hydrophobic polymer (B) may be crosslinked. The glass transition temperature of the hydrophobic polymer (B) is determined by a method as described later in the Examples.

It is preferred that the hydrophobic polymer (B) contains a structural unit derived from a hydrophobic unsaturated monomer (b). It is preferred that the hydrophobic unsaturated monomer (b) has a hydrocarbon chain preferably having 1 to 45 carbon atoms, and more preferably 1 to 24 carbon atoms. The hydrocarbon chain may be either linear or branched. In addition, a hydrocarbon group having a monocyclic or polycyclic aliphatic ring or aromatic ring may also be contained. In addition, a hydrocarbon group having, as a substituent, a linear or branched alkyl group may be further contained in the ring.

Specifically, examples of the hydrophobic unsaturated monomer (b) include methyl (meth)acrylate, ethyl (meth) acrylate, 3-methoxyethyl (meth)acrylate, propyl (meth)acrylate, isopropyl (meth)acrylate, n-butyl (meth)acrylate, isobutyl (meth)acrylate, tert-butyl (meth)acrylate, hexyl (meth)acrylate, 2-ethylhexyl (meth)acrylate, lauryl (meth) acrylate, stearyl (meth)acrylate, 2-phenylethyl (meth)acrylate, benzyl (meth)acrylate, tetradecyl (meth)acrylate, diethylaminoethyl (meth)acrylate, diisopropylaminoethyl (meth) acrylate, and the like. Incidentally, in the present specification, the "(meth)acrylate" expresses at least one of "acrylate" and "methacrylate".

It is preferable that the hydrophobic unsaturated monomer (b) is an alkyl (meth)acrylate having a hydrocarbon chain having 1 to 45 carbon atoms. In the foregoing range of the carbon number, in the case where the glass transition temperature (Tg) of the polymer after the polymerization is low, a soft film can be formed, whereas in the case of using a monomer having a high Tg, a hard film can be formed. By using an alkyl (meth)acrylate having a hydrocarbon chain having the foregoing carbon number range, it is possible to form a film in conformity with a desired styling power.

In addition, a functional group-containing monomer (c) may be copolymerized with the above-described hydrophobic unsaturated monomer (b). Examples of the monomer (c) containing functional group include a monomer having two or more vinyl groups in a molecular structure thereof, a monomer containing a glycidyl group, a monomer containing an allyl group, a monomer containing a hydrolyzable silyl group, a monomer containing an acetoacetyl group, a monomer containing a hydroxyl group, a monomer containing a carboxyl group, and the like.

Of these, it is preferred that a monomer having two or more vinyl groups in a molecular structure thereof or a monomer containing a hydrolyzable silyl group is copolymerized from the standpoint that the water washability is improved without deteriorating the hairdressing properties.

Examples of the monomer having two or more vinyl groups in a molecular structure thereof include divinylbenzene, diallyl phthalate, triallyl cyanurate, triallyl isocyanurate, ethylene glycol di(meth)acrylate, 1,2-propylene glycol di(meth)acrylate, 1,3-propylene glycol di(meth)acrylate, 1,4-butanediol di(meth)acrylate, 1,6-hexanediol di(meth) acrylate, neopentyl glycol di(meth)acrylate, trimethylolpropane tri(meth)methacrylate, allyl (meth)acrylate, and the like.

Of these, ethylene glycol di(meth)acrylate, 1,2-propylene glycol di(meth)acrylate, 1,3-propylene glycol di(meth)acrylate, 1,4-butanediol di(meth)acrylate, 1,6-hexanediol di(meth)acrylate, neopentyl glycol di(meth)acrylate, or trimethylolpropane tri(meth)acrylate is preferred from the standpoint of copolymerizability with the (meth)arylate-based monomer.

Examples of the monomer containing a glycidyl group include glycidyl (meth)acrylate, glycidyl (meth)allyl ether, 3,4-epoxycyclohexyl (meth)acrylate, and the like.

Examples of the monomer containing an allyl group include a monomer having two or more allyl groups, such as triallyloxyethylene, diallyl maleate, triallyl cyanurate, triallyl isocyanurate, tetraallyloxyethane, trimethylolpropane diallyl ether, pentaerythritol triallyl ether, etc., allyl glycidyl ether, allyl acetate, and the like.

Examples of the monomer containing a hydrolyzable silyl group include monomers containing vinyl-based silyl group, such as vinyltrimethoxysilane, vinyltriethoxysilane, vinyltris(β-methoxyethoxy)silane, vinylmethyldimethoxysilane, etc.; and monomers containing (meth)acryloxy-based silyl group, such as γ-(meth)acryloxypropyltrimethoxysilane, γ-(meth)acryloxypropylmethyldimethoxysilane, γ-(meth) acryloxypropyltriethoxysilane, γ-(meth)acryloxypropylmethyldiethoxysilane, etc. Of these, monomers containing (meth)acryloxy-based silyl group are preferred from the standpoint of excellent copolymerizability with the hydrophobic unsaturated monomer (b). Incidentally, in the present specification, the "(meth)acryloxy" expresses at least one of "acryloxy" and "methacryloxy".

Examples of the monomer containing an acetoacetyl group include vinyl acetoacetate, allyl acetoacetate, allyl diacetoacetate, acetoacetoxyethyl (meth)acrylate, acetoacetoxyethyl crotonate, acetoacetoxypropyl (meth)acrylate, acetoacetoxypropyl crotonate, 2-cyanoacetoacetoxyethyl (meth)acrylate, and the like.

Examples of the monomer containing a hydroxyl group include (meth)acrylates, such as 2-hydroxyethyl (meth)acrylate, hydroxypropyl (meth)acrylate, 4-hydroxybutyl (meth) acrylate, etc.; and the like. Of these, 2-hydroxyethyl acrylate or 2-hydroxyethyl methacrylate is preferred from the viewpoints of protective colloid action at the time of emulsion polymerization and water washability.

Examples of the monomer containing a carboxyl group include (meth)acrylic acid, an acrylic acid dimer, crotonic acid, maleic acid, maleic anhydride, fumaric acid, citraconic acid, glutaconic acid, itaconic acid, acrylamide N-glycolic acid, cinnamic acid, and the like. Of these, acrylic acid or methacrylic acid is preferred from the viewpoints of protective colloid action at the time of emulsion polymerization and water washability.

A content proportion of the monomer (c) containing the functional group is preferably 10% by weight or less, more preferably 5% by weight or less, and still more preferably 3% by weight or less relative to the whole of the monomer components. By regulating the content to this range, the matter that the hydrophobic polymer (B) becomes excessively hard is inhibited, a sufficient adhesiveness is exhibited, and the hairdressing properties can be more improved. In addition, from the viewpoint of sufficiently obtaining an improving effect of water washability, the content proportion of the monomer (c) containing the functional group is preferably 0.01% by weight or more, more preferably 0.05% by weight or more, and still more preferably 0.1% by weight or more relative to the whole of the monomer components.

In addition, in the case where the monomer (c) containing the functional group is a monomer having two or more vinyl groups in a molecular structure thereof, the content thereof is preferably 0.01 to 5% by weight, more preferably 0.05 to 3% by weight, and still more preferably 0.1 to 1% by weight relative to the whole of the monomer components.

In addition, besides, in a range where the effects of the present invention are not impaired, a small amount of styrene or a styrene-based monomer, such as α-methylstyrene, etc., or a vinyl ester-based monomer, such as vinyl formate, vinyl acetate, vinyl propionate, vinyl valerate, vinyl butyrate, vinyl isobutyrate, vinyl pivalate, vinyl caprylate, vinyl laurate, vinyl stearate, vinyl benzoate, vinyl versatate, vinyl 2-ethylhexanoate, etc., may be used.

In the aqueous polymer emulsion of the present invention, in addition to the above-described monomer components, other component can be further used, if desired. Such other component may be properly selected according to the purpose, and examples thereof include a polymerization initiator, a polymerization modifier, a co-emulsifier, a plasticizer, and the like.

As the polymerization initiator, those which can be used for usual emulsion polymerization can be used. Examples thereof include an inorganic peroxide, such as potassium persulfate, sodium persulfate, ammonium persulfate, etc.; an organic peroxide; an azo-based initiator; a redox polymerization initiator composed of a peroxide, such as hydrogen peroxide, butyl peroxide, etc., in combination with a reducing agent, such as acidic sodium sulfite, L-ascorbic acid, etc.; and the like. These can be used alone or in combination of two or more thereof. Of these, ammonium persulfate or potassium persulfate is preferred from the standpoint that the polymerization is easy.

The polymerization modifier can be properly selected among those which are known. Examples of such a polymerization modifier include a chain transfer agent, a buffer, and the like.

Examples of the chain transfer agent include alcohols, such as methanol, ethanol, propanol, butanol, etc.; aldehydes, such as acetaldehyde, propionaldehyde, n-butylaldehyde, furfural, benzaldehyde, etc.; mercaptans, such as dodecyl mercaptan, lauryl mercaptan, normal mercaptan, thioglycolic acid, octyl thioglycolate, thioglycerol, etc.; and the like. These can be used alone or in combination of two or more thereof. The use of the chain transfer agent is effective from the standpoint that the polymerization is stably achieved, and it is preferred to use the chain transfer agent for the purpose of regulating a degree of polymerization of the hydrophobic polymer (B).

As the co-emulsifier, any materials which are known to be usable for the emulsion polymerization by a person skilled in the art can be used. Accordingly, the co-emulsifier can be properly selected among known materials, for example, anionic, cationic, and nonionic surfactants, water-soluble polymers having a protective colloid ability other than the amphoteric polymer (A), water-soluble oligomers, and the like.

Examples of the surfactant include anionic surfactants, such as sodium lauryl sulfate, sodium dodecyl benzenesulfonate, etc.; and nonionic surfactants, such as those having a Pluronic type structure, those having a polyoxyethylene type structure, etc. Of these surfactants, among ionic surfactants, especially anionic surfactants, anionic surfactants, such as sodium stearoylmethyl taurate, sodium stearoyl glutamate, sodium stearoyl lactate, etc., are preferred. In addition, as the surfactant, a reactive surfactant having a radical polymerizable unsaturated bond in a structure thereof can also be used. These can be used alone or in combination of two or more thereof.

The use of the surfactant has an effect for smoothly advancing or easily controlling the emulsion polymerization (effect as an emulsifier), or suppressing the generation of coarse particles or the generation of a block-like material during the polymerization. However, when a large amount of such a surfactant is used as an emulsifier, there is a possibility that the shell is separated from the core. For that reason, in the case of using the surfactant, it is preferred that the use amount thereof is an auxiliary amount against the amphoteric polymer (A), namely, the use amount is made small as far as possible.

The core part of the core-shell type polymer particle of the present invention can be selected from the hydrophobic polymer (B). According to this, at the time when a hair cosmetic using the core-shell type polymer particle of the present invention is used for the hair, the touch feeling or softness or the like can be regulated.

<Core-Shell Type Polymer Particle>

The core-shell type polymer particle of the present invention has the above-described shell part and the above-described core part. According to this, it is possible to provide the softness of touch with realizing the hardness necessary for a hair cosmetic, especially a hairdressing agent.

As an analysis method of the core-shell structure of the core-shell type polymer particle of the present invention, for example, TEM (transmission electron microscope) can be used. The observation can be performed by applying the aqueous polymer emulsion of the present invention on a carbon support film and then drying. It is preferred to dye the core-shell type polymer particle with osmium tetroxide, ruthenium tetroxide, chlorosulfonic acid/uranyl acetate, silver sulfide, or the like. In this case, the contrast can be made large.

From the viewpoints of improving the suppleness, the softness, and the humidity resistance at higher levels and more preventing the generation of flaking from occurring, a mass ratio of the amphoteric polymer (A) to the hydrophobic polymer (B) [(A)/(B)] in the core-shell type polymer particle is preferably 1/10 to 10/1. In addition, in this case, there is a tendency that the polymerization is easy to be stably advanced; there is a tendency that coarse particles or block-like polymer pieces are hardly generated during the polymerization; and there is a tendency that the storage stability of the aqueous polymer emulsion is improved. Furthermore, there is a tendency that the hair washability is improved.

The mass ratio of the amphoteric polymer (A) to the hydrophobic polymer (B) [(A)/(B)] is more preferably from 1/5 to 5/1. By completing the polymerization within this range, an effect for making the particles uniform is exhibited, and it becomes possible to obtain an emulsion solution with excellent storage stability. In addition, the emulsion is excellent in transparency or uniformity at the time of film formation, and even in the case of applying to the hair, it becomes possible to realize styling having both flexibility and suppleness. In addition, it is possible to much more prevent the generation of flaking from occurring.

<Aqueous Polymer Emulsion>

The aqueous polymer emulsion of the present invention is one in which the core-shell type polymer of the present invention is dispersed in water. From the viewpoints of stability of the emulsion and smoothness and transparency of the formed film, an average particle diameter of the core-shell type polymer particle in the aqueous polymer emulsion is preferably from 10 nm to 10 μm, more preferably from 10 to 500 nm, and still more preferably from 10 to 300 nm.

As shown in the Examples as described later, the core-shell type polymer particle of the present invention is produced as the above-described aqueous polymer emulsion dispersed in water and used. By drying this aqueous polymer emulsion by means of freeze drying or the like, a powdered core-shell type polymer particle can also be obtained. In this case, since the volume or weight at the time of transportation can be made small, the transportation becomes easy, so that it can be devised to reduce the transportation costs. By dispersing the powdered core-shell type polymer particle, the aqueous polymer emulsion is obtained.

<Hair Cosmetic Composition>

The hair cosmetic composition of the present invention is one including the above-described aqueous polymer emulsion blended therein. In a hair cosmetic composition, in addition to the aqueous polymer emulsion, components which are used for usual cosmetics may be properly blended with a range where the effects of the present invention are not impaired.

As such a component, for example, glycerides, such as camellia oil, castor oil, cacao oil, mink oil, avocado oil, jojoba oil, macadamia nut oil, olive oil, etc.; waxes, such as beeswax, lanolin, etc.; hydrocarbons, such as liquid paraffin, solid paraffin, isoparaffin, squalane, etc.; linear or branched higher alcohols, such as cetyl alcohol, oleyl alcohol, stearyl alcohol, isostearyl alcohol, lauryl alcohol, 2-octyl decanol, etc.; polyhydric alcohols, such as ethylene glycol, polyethylene glycol, propylene glycol, polypropylene glycol, glycerin, sorbitol, etc.; ethylene oxide and/or propylene oxide adducts of a higher alcohol, such as polyoxyethylene lauryl ether, polyoxypropylene cetyl alcohol, polyoxyethylene polyoxypropylene stearyl ether, etc.; esters, such as isopropyl myristate, octyldodecyl myristate, hexyl laurate, cetyl lactate, etc.; amides, such as oleic acid diethanolamide, lauric acid diethanolamide, etc.; silicone derivatives, such as dimethylpolysiloxane, methylphenyl polysiloxane, polyether-modified silicone, amino-modified silicone, etc.; cationic surfactants, such as stearyltrimethylammonium chloride, distearyldimethylammonium chloride, lauryltrimethylammonium chloride, etc.; anionic surfactants, such as polyoxyethylene lauryl ether sulfate, polyoxyethylene lauryl sulfosuccinate, etc.; amphoteric surfactants, such as lauryl hydroxysulfobetaine, lauryl dimethylcarboxybetaine, etc.; protein derivatives or amino acid derivatives, such as a collagen hydrolyzate, a keratin hydrolyzate, a polyamino acid, etc.; UV absorbers, such as plant extracts, crude drugs, vitamins, oxybenzene, etc.; chelating agents, such as EDTA-Na, etc.; antiseptics, such as paraben, etc.; antioxidants; coloring matters; pigments; flavors; and so on may be properly blended within a range where the effects of the present invention are not impaired.

The hair cosmetic composition of the present invention is not particularly limited with respect to an application thereof, and for example, it may be used as a hairdressing agent, a setting agent, a shampoo, a rinse, a conditioner, or a hair treatment. Of these, a hairdressing agent or a setting agent is preferred. This is because when the amphoteric polymer (A) is used in the shell part of the core-shell type polymer particle of the present invention, a setting power or a holding power is revealed. In the case where the polymer in the shell part is a cationic polymer, there are a lot of cationic polymers which have a high affinity with the hair but do not harm a feeling of the hair. Therefore, while such a cationic polymer is suitable as a coloring agent, a rinse, a conditioner, or a hair treatment, in general, it is hardly used as a hairdressing agent.

The hair cosmetic composition of the present invention is not particularly limited with respect to a form of use, and it can be, for example, used as an aerosol hair spray, a pump type hair spray, a foam type hair spray, a hair mist, a setting lotion, a hair gel, a hair cream, a hair oil, or the like.

The hair cosmetic can also be formed in an aerosol agent type according to the usual way by using, as a propellant, a chlorofluoroalkane, such as trichloromonofluoromethane, dichlorodifluoromethane, etc.; a liquefied petroleum gas composed of an alkane; dimethyl ether; a compressed gas, such as a carbon dioxide gas and a nitrogen gas; or the like, or a mixed gas thereof. Besides the hair cosmetic, the composition of the present invention can also be used for skin care, sun care, makeup, or the like.

EXAMPLES

Although the present invention is more specifically described below based on the Examples, it should be construed that the present invention is by no means limited by the following Examples.

Example 1

Example of an aqueous polymer emulsion in which a core-shell type polymer particle having a core part composed of a hydrophobic polymer and a shell part covering this core part and composed of an amphoteric polymer is dispersed in water is described. The aqueous polymer emulsion of the present Example was produced in the following manner.

First of all, YUKAFORMER AMPHOSET, manufactured by Mitsubishi Chemical Corporation was prepared as an amphoteric polymer. This is hereunder referred to as "Amphoteric Polymer I". Subsequently, in a reactor equipped with a reflux condenser, a dropping pump, a thermometer, a nitrogen gas introducing pipe, and a stirring device, 22.5 g of Amphoteric Polymer I and 70 g of water were added to prepare an aqueous phase, and this aqueous phase was heated to 60° C. in a nitrogen atmosphere.

Subsequently, 0.64 g of a 70% by mass t-butyl hyperoxide aqueous solution (initiator) was diluted with 5.8 g of water to prepare an initiator diluted solution, and this initiator diluted solution was added to the aqueous phase. Thereafter, 0.23 g of ascorbic acid was diluted with water to prepare a 1% by mass ascorbic acid aqueous solution, and this ascorbic acid aqueous solution was added to the aqueous phase, followed by thoroughly stirring.

In addition, 22.5 g of Amphoteric Polymer I and 45 g of butyl acrylate (BA) were mixed to prepare a uniform oil phase. To this oil phase, 70 g of water was added, and the contents were stirred with a homomixer at a rotation speed of 3,000 rpm for 5 minutes, to obtain a pre-emulsion.

Subsequently, the pre-emulsion was dropped in the aqueous phase at a temperature of 60° C. within the reactor over 1 hour by the dropping pump. Subsequently, the temperature within the reactor was elevated to 65° C., and the contents were polymerized for 3 hours, to obtain an aqueous polymer emulsion.

This aqueous polymer emulsion was one in which the core-shell type polymer particle having a core part composed of polybutyl acrylate (BA) and a shell part covering this core part and composed of Amphoteric Polymer I was dispersed in water.

The kind and blending proportion of the amphoteric polymer forming the shell part in the core-shell type polymer particle in the present Example are shown in Table 1 as described later. In addition, the kind and blending proportion of the monomer [(meth)acrylic acid ester] constituting the hydrophobic polymer forming the core part in the core-shell type polymer particle are shown in Table 1 as described later.

Furthermore, a mass ratio of the amphoteric polymer (A) forming the shell part to the hydrophobic polymer (B) forming the core part [(A)/(B)] is shown in Table 1 as described later. In this connection, a viscosity of the aqueous polymer emulsion at 25° C. was 12 mPa·s.

Subsequently, an average particle diameter of the core-shell type polymer particle in the aqueous polymer emulsion was measured. The results are shown in Table 1 as described later. The average particle diameter was a particle diameter at a volume integrated value of 50% in the particle size distribution determined by the laser diffraction and scattering method and measured with a laser diffraction particle size distribution analyzer (Nanotrac 150, manufactured by Nikkiso Co., Ltd.).

In addition, a glass transition temperature Tg (° C.) of the polymer (acrylic resin) forming the core part of the core-shell type polymer particle was calculated. The Tg of the polymer of the core part is a theoretical calculation value as determined according to the FOX equation represented by the following equation (1).

$$1/Tg = W1/Tg1 + W2/Tg2 + \ldots + Wn/Tgn \quad (1)$$

In the formula (1), Tg is a glass transition temperature of the polymer (acrylic resin) forming the core part; W1, W2, . . . , Wn are each a weight fraction of each of the monomers constituting the polymer; and Tg1, Tg2, . . . , Tg n are each a glass transition temperature of each of homopolymers of the monomers.

As the glass transition temperatures of the homopolymers, known literature values can adopted. Specifically, these glass transition temperatures are described in, for example, *Acrylic Ester Catalogue* of Mitsubishi Rayon Co., Ltd. (1977 Version); Kyozo Kitaoka, "Shin Kobunshi Bunko 7, Guide to Synthetic Resin, for Coating Material", Kobunshi Kankokai, published in 1997, pp. 168-169; and so on.

Example 2

An aqueous polymer emulsion was prepared in the same manner as in Example 1, except that in the preparation of the oil phase in Example 1, 45 g of butyl acrylate (BA) used was changed to 8.8 g of methyl methacrylate (MMA), 20.5 g of butyl acrylate (BA), and 15.7 g of isobutyl methacrylate (i-BMA).

The aqueous polymer emulsion of the present Example was one in which the core-shell type polymer particle having a core part composed of poly(methyl methacrylate/butyl acrylate/isobutyl methacrylate), and a shell part composed of Amphoteric Polymer I which is same as in Example 1 was dispersed in water. The composition and physical properties, and so on of the core-shell type polymer particle in the aqueous polymer emulsion of the present Example are shown in Table 1 as described later in the same manner as in Example 1.

Example 3

An aqueous polymer emulsion was prepared in the same manner as in Example 1, except that in the preparation of the oil phase in Example 1, 45 g of butyl acrylate (BA) used was changed to 28.4 g of methyl methacrylate (MMA), 12.1 g of butyl acrylate (BA), and 4.5 g of stearyl methacrylate (SMA).

The aqueous polymer emulsion of the present Example was one in which the core-shell type polymer particle having a core part composed of poly(methyl methacrylate/butyl acrylate/stearyl methacrylate), and a shell part composed of Amphoteric Polymer I which is same as in Example 1 was dispersed in water. The composition and physical properties, and so on of the core-shell type polymer particle in the aqueous polymer emulsion of the present Example are shown in Table 1 as described later in the same manner as in Example 1.

Example 4

To prepare an aqueous phase, 22.5 g of Amphoteric Polymer I and 70 g of water used for the preparation of the aqueous phase in Example 1 were changed to 37.5 g of Amphoteric Polymer II (YUKAFORMER 510, manufactured by Mitsubishi Chemical Corporation) and 60 g of water, respectively.

In addition, in the preparation of the oil phase in Example 1, 22.5 g of Amphoteric Polymer I used was changed to 37.5 g of Amphoteric Polymer II, and 45 g of butyl acrylate (BA) used was changed to 31.5 g of methyl methacrylate (MMA) and 13.5 g of 2-ethylhexyl acrylate (2EHA), to prepare an oil phase. Furthermore, the amount of water to be added to the oil phase was changed to 60 g, to prepare a pre-emulsion. Besides, the same procedures as in Example 1 were followed to prepare an aqueous polymer emulsion.

The aqueous polymer emulsion of the present Example was one in which the core-shell type polymer particle having a core part composed of poly(methyl methacrylate/2-ethylhexyl acrylate) and a shell part composed of Amphoteric Polymer II was dispersed in water. The composition and physical properties, and so on of the core-shell type polymer particle in the aqueous polymer emulsion of the present Example are shown in Table 1 as described later in the same manner as in Example 1.

Example 5

In the preparation of the aqueous phase in Example 1, 22.5 g of Amphoteric Polymer I and 70 g of water used were changed to 132.35 g of Amphoteric Polymer III (YUKAFORMER 204WL-2, manufactured by Mitsubishi Chemical Corporation) and 5.0 g of water, respectively, to prepare an aqueous phase.

In addition, in the preparation of the oil phase in Example 1, 22.5 g of Amphoteric Polymer I used was changed to 132.35 g of Amphoteric Polymer III, and 45 g of butyl acrylate (BA) used was changed to 31.5 g of methyl methacrylate (MMA) and 13.5 g of butyl acrylate (BA), to prepare an oil phase. Furthermore, the amount of water to be added to the oil phase was changed to 5.0 g, to prepare a pre-emulsion. Besides, the same procedures as in Example 1 were followed to prepare an aqueous polymer emulsion.

The aqueous polymer emulsion of the present Example was one in which the core-shell type polymer particle having a core part composed of poly(methyl methacrylate/butyl acrylate) and a shell part composed of Amphoteric Polymer III was dispersed in water. The composition and physical properties, and so on of the core-shell type polymer particle in the aqueous polymer emulsion of the present Example are shown in Table 1 as described later in the same manner as in Example 1.

Example 6

In the preparation of the aqueous phase in Example 1, 22.5 g of Amphoteric Polymer I and 70 g of water used were changed to 26.5 g of Amphoteric Polymer III (YUKAF- ORMER 204WL-2, manufactured by Mitsubishi Chemical Corporation) and 43.2 g of water, respectively, to prepare an aqueous phase.

In addition, in the preparation of the oil phase in Example 1, 22.5 g of Amphoteric Polymer I used was changed to 26.5 g of Amphoteric Polymer III, and 45 g of butyl acrylate (BA) used was changed to 31.5 g of methyl methacrylate (MMA) and 13.5 g of butyl acrylate (BA), to prepare an oil phase. Furthermore, the amount of water to be added to the oil phase was changed to 43.2 g, to prepare a pre-emulsion. Besides, the same procedures as in Example 1 were followed to prepare an aqueous polymer emulsion.

The aqueous polymer emulsion of the present Example was one in which the core-shell type polymer particle having a core part composed of poly(methyl methacrylate/butyl acrylate) and a shell part composed of Amphoteric Polymer III was dispersed in water. The composition and physical properties, and so on of the core-shell type polymer particle in the aqueous polymer emulsion of the present Example are shown in Table 1 as described later in the same manner as in Example 1.

Example 7

In the preparation of the aqueous phase in Example 1, 22.5 g of Amphoteric Polymer I and 70 g of water used were changed to 37.5 g of Amphoteric Polymer IV (DIA-FORMER Z-632, manufactured by Mitsubishi Chemical Corporation) and 60 g of water, respectively, to prepare an aqueous phase.

In addition, in the preparation of the oil phase in Example 1, 22.5 g of Amphoteric Polymer I used was changed to 37.5 g of Amphoteric Polymer IV, and 45 g of butyl acrylate (BA) used was changed to 31.5 g of methyl methacrylate (MMA) and 13.5 g of butyl acrylate (BA), to prepare an oil phase. Furthermore, the amount of water to be added to the oil phase was changed to 60 g, to prepare a pre-emulsion.

Besides, the same procedures as in Example 1 were followed to prepare an aqueous polymer emulsion. The aqueous polymer emulsion of the present Example was one in which the core-shell type polymer particle having a core part composed of poly(methyl methacrylate/butyl acrylate) and a shell part composed of Amphoteric Polymer IV was dispersed in water. The composition and physical properties, and so on of the core-shell type polymer particle in the aqueous polymer emulsion of the present Example are shown in Table 1 as described later in the same manner as in Example 1.

Example 8

In the preparation of the oil phase in Example 1, 45 g of butyl acrylate (BA) used was changed to 6.75 g of methyl methacrylate (MMA), 15.75 g of butyl acrylate (BA), and 22.5 g of stearyl methacrylate (SMA), to prepare an oil phase. Besides, the same procedures as in Example 1 were followed to prepare an aqueous polymer emulsion.

The aqueous polymer emulsion of the present Example was one in which the core-shell type polymer particle having a core part composed of poly(methyl methacrylate/butyl acrylate/stearyl methacrylate) and a shell part composed of Amphoteric Polymer I was dispersed in water. The composition and physical properties, and so on of the core-shell type polymer particle in the aqueous polymer emulsion of the present Example are shown in Table 1 as described later in the same manner as in Example 1.

Example 9

In the preparation of the oil phase in Example 1, 45 g of butyl acrylate (BA) used was changed to 45 g of methyl methacrylate (MMA), to prepare an oil phase. Besides, the same procedures as in Example 1 were followed to prepare an aqueous polymer emulsion. The aqueous polymer emulsion of the present Example was one in which the core-shell type polymer particle having a core part composed of polymethyl methacrylate and a shell part composed of Amphoteric Polymer I was dispersed in water. The composition and physical properties, and so on of the core-shell type polymer particle in the aqueous polymer emulsion of the present Example are shown in Table 1 as described later in the same manner as in Example 1.

Example 10

First of all, a polymer composed of, as essential components, both of an unsaturated monomer containing a carboxyl group and an unsaturated monomer containing a tertiary amino group, which is a hydroxypropyl acrylate/butylaminoethyl methacrylate/octylamide acrylate copolymer (UNFOAMER 28-4910, manufactured by National Starch), was dissolved in an ethanol solution.

Subsequently, 90% of 100% of an acid equivalent of the polymer in the resulting solution was neutralized with 2-amino-2-methyl-1-propanol and regulated such that a polymer solid content of UNFOAMER 28-4910 was 30% by mass, to obtain Amphoteric Polymer V.

Subsequently, in the preparation of the aqueous phase in Example 1, 22.5 g of Amphoteric Polymer I and 70 g of water used were changed to 37.5 g of Amphoteric Polymer V and 60 g of water, respectively, to prepare an aqueous phase. In addition, in the preparation of the oil phase in Example 1, 22.5 g of Amphoteric Polymer I used was changed to 37.5 g of Amphoteric Polymer V, and 45 g of butyl acrylate (BA) used was changed to 31.5 g of methyl methacrylate (MMA) and 13.5 g of butyl acrylate (BA), to prepare an oil phase. Furthermore, the amount of water to be added to the oil phase was changed to 60 g, to prepare a pre-emulsion. Besides, the same procedures as in Example 1 were followed to prepare an aqueous polymer emulsion.

The aqueous polymer emulsion of the present Example was one in which the core-shell type polymer particle having a core part composed of poly(methyl methacrylate/butyl acrylate) and a shell part composed of Amphoteric Polymer V was dispersed in water. The composition and physical properties, and so on of the core-shell type polymer particle in the aqueous polymer emulsion of the present Example are shown in Table 1 as described later in the same manner as in Example 1.

Example 11

In the preparation of the aqueous phase in Example 1, 22.5 g of Amphoteric Polymer I and 70 g of water used were changed to 54 g of Amphoteric Polymer I and 45 g of water, respectively, to prepare an aqueous phase. In addition, a solution prepared by diluting 0.06 g of 70% by mass of a t-butyl hydroperoxide aqueous solution (initiator) with 0.6 g of water was used as an initiator diluted solution, and this was added to the aqueous phase.

In addition, a solution prepared by diluting 0.02 g of ascorbic acid with water was used as a 1% by mass ascorbic acid aqueous solution, and this was added to the aqueous phase. In addition, in the preparation of the oil phase in Example 1, 22.5 g of Amphoteric Polymer I used was changed to 54 g of Amphoteric Polymer I, and 45 g of butyl acrylate (BA) used was changed to 3.15 g of methyl methacrylate (MMA) and 1.35 g of butyl acrylate (BA), to prepare an oil phase. Furthermore, the amount of water to be added to the oil phase was changed to 45 g, to prepare a pre-emulsion. Besides, the same procedures as in Example 1 were followed to prepare an aqueous polymer emulsion.

The aqueous polymer emulsion of the present Example was one in which the core-shell type polymer particle having a core part composed of poly(methyl methacrylate/butyl acrylate) and a shell part composed of Amphoteric Polymer I was dispersed in water. The composition and physical properties, and so on of the core-shell type polymer particle in the aqueous polymer emulsion of the present Example are shown in Table 1 as described later in the same manner as in Example 1.

Example 12

In the preparation of the aqueous phase in Example 1, 22.5 g of Amphoteric Polymer I and 70 g of water used were changed to 7.5 g of Amphoteric Polymer I and 60 g of water, respectively, to prepare an aqueous phase. In addition, in the preparation of the oil phase in Example 1, 22.5 g of Amphoteric Polymer I used was changed to 7.5 g of Amphoteric Polymer I, and 45 g of butyl acrylate (BA) used was changed to 31.5 g of methyl methacrylate (MMA) and 13.5 g of butyl acrylate (BA), to prepare an oil phase. Furthermore, the amount of water to be added to the oil phase was changed to 60 g, to prepare a pre-emulsion. Besides, the same procedures as in Example 1 were followed to prepare an aqueous polymer emulsion.

The aqueous polymer emulsion of the present Example was one in which the core-shell type polymer particle having a core part composed of poly(methyl methacrylate/butyl acrylate) and a shell part composed of Amphoteric Polymer I was dispersed in water. The composition and physical properties, and so on of the core-shell type polymer particle in the aqueous polymer emulsion of the present Example are shown in Table 1 as described later in the same manner as in Example 1.

Comparative Example 1

In the preparation of the aqueous phase in Example 1, 22.5 g of Amphoteric Polymer I and 70 g of water used was changed to a 30% by mass solution prepared by dissolving 11.25 g of polyvinylpyrrolidone (PVP) (Luviskol K90 Powder, manufactured by BASF SE) in 26.25 g of ethanol and 60 g of water, respectively, to prepare an aqueous phase.

In addition, in the preparation of the oil phase in Example 1, 22.5 g of Amphoteric Polymer I used was changed to a 30% by mass solution prepared by dissolving 11.25 g of PVP in 26.25 g of ethanol, and 45 g of butyl acrylate (BA) used was changed to 31.5 g of methyl methacrylate (MMA) and 13.5 g of butyl acrylate (BA), to prepare an oil phase. Furthermore, the amount of water to be added to the oil phase was changed to 60 g, to prepare a pre-emulsion. Besides, the same procedures as in Example 1 were followed to prepare an aqueous polymer emulsion.

The aqueous polymer emulsion of the present Example was one in which the core-shell type polymer particle having a core part composed of poly(methyl methacrylate/butyl acrylate) and a shell part composed of PVP was dispersed in water. The composition and physical properties, and so on of the core-shell type polymer particle in the aqueous polymer emulsion of the present Example are shown in Table 1 as described later in the same manner as in Example 1.

Comparative Example 2

An amphoteric polymer "YUKAFORMER 510" (manufactured by Mitsubishi Chemical Corporation) was used in place of the aqueous polymer emulsion of Example 1. Namely, Comparative Example 2 is composed of the amphoteric polymer and does not have a core-shell type structure.

Experimental Examples

Using each of the aqueous polymer emulsions of Examples 1 to 12 and Comparative Example 1 and the amphoteric polymer of Comparative Example 2, a film was formed on the hair and evaluated for hardness, suppleness, humidity resistance, and flaking of the film and also evaluated for washability in the following manners. The results are shown in Table 1.

"Hardness"

The hardness of the hair having a film formed thereon was evaluated by performing the three-point bending test in conformity with JIS K7171 (2008). Specifically, first of all, 0.4 g of each of the aqueous polymer emulsions of Examples 1 to 12 and Comparative Example 1 (aqueous solutions having a solid content of 5% by mass) and the amphoteric polymer of Comparative Example 2 was applied onto a hair bundle of hair having a length of 15 cm and a weight of 1.3 g.

Subsequently, the hair bundle was combed with a comb and formed in a plate-like state having a width of 2 cm, which was then dried at 50° C. for 2 hours to form a film. There was thus obtained a plate-like hair having the film formed on a surface thereof. Subsequently, the hair was allowed to stand for 24 hours under a condition at 23° C. and a relative humidity of 60%. Thereafter, the plate-like hair was placed on a support table having a supporting point distance of 65 mm, and a central part of the hair was pressed by an indenter at a rate of 2 cm/sec (three-point bending test). Then, a maximum load (bending strength) at a point of time when the central part of the hair was bent to a depth of 2 cm was measured.

The case where the maximum load is 100 g or more was evaluated as "A"; the case where the maximum load is 70 g or more and less than 100 g was evaluated as "B"; the case where the maximum load is 50 g or more and less than 70 g was evaluated as "C"; and the case where the maximum load is less than 50 g was evaluated as "D".

"Suppleness"

The suppleness was evaluated by measuring a bending strength of the hair bundle after breaking the film. Specifically, the hair bundle after measuring the bending strength in the above-described evaluation of hardness was placed on a rectangular edge and pulled at a rate of about 15 cm/sec with holding with a hand, thereby breaking the hair bundle. Thereafter, the three-point bending test was performed in the same manner as in the above-described evaluation of hardness, to measure the bending strength (maximum load) of the hair bundle.

Then, the case where the load is 40 g or more was evaluated as "A"; the case where the load is 30 g or more and less than 40 g was evaluated as "B"; the case where the load is 20 g or more and less than 30 g was evaluated as "C"; and the case where the load is less than 20 g was evaluated as "D".

"Softness"

Each of the aqueous polymer emulsions of Examples 1 to 12 and Comparative Example 1 (aqueous solutions having a solid content of 5% by mass) and the amphoteric polymer of Comparative Example 2 was subjected to an actual use test. As for the solution, the softness after application was evaluated by 10 expert panels.

The case where less than 2 panels perceived that after the application, the softness was not felt was evaluated as "A"; the case where 2 or more and less than 4 panels perceived that after the application, the softness was not felt was evaluated as "B"; the case where 4 or more and less than 7 panels perceived that after the application, the softness was not felt was evaluated as "C"; and the case where 7 or more panels perceived that after the application, the softness was not felt was evaluated as "D".

"Humidity Resistance"

The humidity resistance was evaluated by measuring a curl retention of the hair having the film formed thereon. 0.7 g of each of the aqueous polymer emulsions of Examples 1 to 12 and Comparative Example 1 (aqueous solutions having a solid content of 5% by mass) and the amphoteric polymer of Comparative Example 2 was applied onto a black virgin hair (length: 23 cm, weight: 2 g), a curl was immediately prepared using a curler having a curl diameter of 1.2 cm, and this was dried at 50° C. for 2 hours.

A length of this curled hair strand was measured. This length is designated as an initial value (L0). Subsequently, the dried hair strand was hung on a memory-provided board and charged in a high temperature and high humidity chamber for 3 hours at a temperature of 30° C. and a relative humidity of 90%, and a length of the hair strand was measured. This length is designated as a length (L1) after humidification. In this connection, when the hair strand is in a curled state, the length of the hair strand is a maximum diameter of the curl, whereas when the curl is partially or wholly loosened, the length of the hair strand is a maximum length from the end of the side of the root of hair (for example, a length of from the end of the side of the root of hair to the tip of hair). Subsequently, a curl retention value was calculated according to the following equation (2). In this connection, it is meant that the curl retention rate is stronger, the humidity resistance is more excellent, and the styling holding power is more excellent as the curl retention value is closer to 100%.

$$\text{Curl retention value (\%)} = 100 \times (23-L1)/(23-L0) \quad (2)$$

Then, the case where the curl retention value is 85% or more was evaluated as "A"; the case where the curl retention value is less than 85% and 70% or more was evaluated as "B"; the case where the curl retention value is less than 70% and 45% or more was evaluated as "C"; and the case where the curl retention value is less than 45% was evaluated as "D".

"Washability"

Each of the aqueous polymer emulsions of Examples 1 to 12 and Comparative Example 1 (25% by mass aqueous solutions) and the amphoteric polymer of Comparative Example 2 was applied on a glass plate using an applicator having a coating film width of 100 μm and then dried at 50° C. for 2 hours, to form a film on the glass plate. Subsequently, the film was held for 24 hours under a condition at 23° C. and a relative humidity of 60%. Thereafter, the film was dipped in warm water at 40° C., and a time until the film was completely dissolved was measured.

Then, the case where the time until dissolution is within 1 minute was evaluated as "A"; the case where the time until dissolution is more than 1 minute and within 3 minutes was evaluated as "B"; the case where the time until dissolution is more than 3 minutes and within 5 minutes was evaluated as "C"; and the case where even when the time exceeds 5 minutes, the film is not completely dissolved was evaluated as "D".

"Flaking"

A predetermined amount of each of the aqueous polymer emulsions of Examples 1 to 12 and Comparative Example 1 and the amphoteric polymer of Comparative Example 2 was applied on a hair bundle of hair and then completely dried. Thereafter, the hair bundle was allowed to pass through a comb, and the amount of a peeled polymer piece existent on the hair was observed with a stereoscopic microscope having a magnification of 20 times, thereby examining the state of flaking.

Then, the case where the peeled polymer piece is not confirmed at all was evaluated as "A"; the case where the peeled polymer piece is not substantially confirmed was evaluated as "B"; the case where the peeled polymer piece is slightly confirmed was evaluated as "C"; and a very large amount of the peeled polymer piece is confirmed was evaluated as "D".

In this connection, in the foregoing, "A" means "very good"; "B" means "good"; "C" means "moderate"; and "D" means "bad".

TABLE 1

|  |  | Example |  |  |  |  |  |  |  |  |  |  |  | Comparative Example |  |
|---|---|---|---|---|---|---|---|---|---|---|---|---|---|---|---|
|  |  | 1 | 2 | 3 | 4 | 5 | 6 | 7 | 8 | 9 | 10 | 11 | 12 | 1 | 2 |
| Amphoteric polymer | Amphoteric Polymer I | 33 | 33 | 33 |  |  |  |  | 33 | 33 |  | 92.3 | 14.3 |  |  |
|  | Amphoteric Polymer II |  |  |  | 33 |  |  |  |  |  |  |  |  |  | 100 |
|  | Amphoteric Polymer III |  |  |  |  | 50 | 16 |  |  |  |  |  |  |  |  |
|  | Amphoteric Polymer IV |  |  |  |  |  |  | 33 |  |  |  |  |  |  |  |
|  | Amphoteric Polymer V |  |  |  |  |  |  |  |  |  | 33 |  |  |  |  |
|  | PVP |  |  |  |  |  |  |  |  |  |  |  |  | 33 |  |
| Acrylate | MMA |  | 13 | 42.2 | 47 | 35 | 58.8 | 47 | 10 | 67 | 47 | 5.4 | 60 | 47 |  |
|  | 2EHA |  |  |  | 20 |  |  |  |  |  |  |  |  |  |  |
|  | BA | 67 | 30.5 | 18.1 |  | 15 | 25.2 | 20 | 23.5 |  | 20 | 2.3 | 25.7 | 20 |  |

TABLE 1-continued

|  |  | Example |  |  |  |  |  |  |  |  |  |  |  | Comparative Example |  |
|---|---|---|---|---|---|---|---|---|---|---|---|---|---|---|---|
|  |  | 1 | 2 | 3 | 4 | 5 | 6 | 7 | 8 | 9 | 10 | 11 | 12 | 1 | 2 |
| Physical properties | i-BMA |  | 23.5 |  |  |  |  |  |  |  |  |  |  |  |  |
|  | SMA |  |  | 7 |  |  |  |  | 33.5 |  |  |  |  |  |  |
|  | Shell/core ratio | ½ | ½ | ½ | ½ | ⅕ | ⅙ | ½ | ½ | ½ | ½ | 12/1 | 1/12 | ½ |  |
|  | Average particle [nm] | 46 | 41 | 48 | 20 | 80 | 170 | 450 | 48 | 47 | 350 | 5427 | 1180 | 3187 |  |
|  | Tg [° C.] | −54 | 5 | 24.8 | 39 | 44.6 | 44.6 | 44.6 | −60 | 105 | 44.6 | 44.6 | 44.6 | 44.6 |  |
| Evaluation results | Hardness | A | A | A | A | A | A | A | A | A | A | A | B | A | B |
|  | Suppleness | A | A | A | A | A | A | A | A | B | B | C | D | D | D |
|  | Softness | A | A | A | A | A | A | A | A | B | B | C | C | C | D |
|  | Humidity resistance | A | A | A | A | A | A | A | A | B | B | C | C | D | B |
|  | Washability | A | A | A | A | A | A | A | A | A | A | B | B | B | B |
|  | Flaking | A | A | A | A | A | A | B | A | B | B | D | D | D | B |

Amphoteric Polymer I: YUKAFORMER AMPHOSET (manufactured by Mitsubishi Chemical Corporation
Amphoteric Polymer II: YUKAFORMER 510 (manufactured by Mitsubishi Chemical Corporation
Amphoteric Polymer III: YUKAFORMER 204WL-2 (manufactured by Mitsubishi Chemical Corporation
Amphoteric Polymer IV: DIAFORMER Z-632 (manufactured by Mitsubishi Chemical Corporation
Amphoteric Polymer V: UNFOAMER 28-4910 (manufactured by National Starch), neutralized with 2-amino-2-methyl-1-propanol in terms of an acid equivalent of 90%
PVP: Polyvinylpyrrolidone (Luviskol K90 Powder, manufactured by BASF SE)

As shown in Table 1, the aqueous polymer emulsions according to the Examples had hardness, suppleness, softness, and humidity resistance. Conventionally, the hardness and the softness were hardly made compatible with each other. As shown in Comparative Example 2, although the polymer which does not have a core-shell type structure had a thorough hardness, it did not exhibit softness. On the other hand, by adopting the core-shell type structure of the present invention, as shown in Examples 1 to 12, the compatibility between hardness and softness was realized. In consequence, the core-shell type polymer particle of the present invention is able to form a film which is easily washed and removed and is suitable as a hair cosmetic composition.

While the invention has been described in detail and with reference to specific embodiments thereof, it will be apparent to one skilled in the art that various changes and modifications can be made therein without departing from the spirit and scope thereof

The invention claimed is:

1. A method of cosmetic treatment of hairs, the method comprising:
   applying a hair cosmetic composition on hairs to form a film on the hairs,
   wherein the hair cosmetic composition comprises an aqueous polymer emulsion comprising a core-shell type polymer particle dispersed in water, and
   wherein the core-shell type polymer particle comprises a shell part comprising an amphoteric ion polymer (A) and a core part comprising a hydrophobic polymer (B).

2. The method according to claim 1, wherein an average particle diameter of the core-shell type polymer particle dispersed in the aqueous polymer emulsion is 10 nm to 10 μm.

3. The method according to claim 1,
   wherein the hair cosmetic composition further comprises an additional component, and
   wherein the additional component is at least one selected from the group consisting of a glyceride, a wax, a hydrocarbon, a linear or branched higher alcohol, a polyhydric alcohol, an ethylene oxide and/or propylene oxide adduct of a higher alcohol, an ester, an amide, a silicone derivative, a cationic surfactant, an anionic surfactant, an amphoteric surfactant, a protein derivative or an amino acid derivative, a UV absorber, a chelating agent, an antiseptic, an antioxidant; a coloring matter; a pigment; a flavor, and a propellant.

4. The method according to claim 2,
   wherein the hair cosmetic composition further comprises an additional component, and
   wherein the additional component is at least one selected from the group consisting of a glyceride, a wax, a hydrocarbon, a linear or branched higher alcohol, a polyhydric alcohol, an ethylene oxide and/or propylene oxide adduct of a higher alcohol, an ester, an amide, a silicone derivative, a cationic surfactant, an anionic surfactant, an amphoteric surfactant, a protein derivative or an amino acid derivative, a UV absorber, a chelating agent, an antiseptic, an antioxidant; a coloring matter; a pigment; a flavor, and a propellant.

5. The method according to claim 1, wherein the amphoteric polymer (A) comprises a repeating unit derived from an unsaturated monomer having a betaine structural group.

6. The method according to claim 1, wherein the amphoteric polymer (A) comprises a repeating unit derived from an unsaturated monomer having an amine oxide group.

7. The method according to claim 1, wherein the amphoteric polymer (A) comprises a repeating unit derived from an unsaturated monomer having an anion group selected from the group consisting of a carboxyl group, a sulfonic acid group, and a phosphoric acid group, and further comprises at least one of a repeating unit derived from an unsaturated monomer having a tertiary amino group and a repeating unit derived from an unsaturated monomer having a quaternary ammonium group.

8. The method according to claim 1, wherein a mass ratio of the amphoteric polymer (A) to the hydrophobic polymer (B) ((A)/(B)) is from 1/10 to 10/1.

9. The method according to claim 1, wherein a glass transition temperature of the hydrophobic polymer (B) is −70° C. or higher and 105° C. or lower.

10. The method according to claim 1, wherein the hydrophobic polymer (B) comprises a structural unit derived from a hydrophobic unsaturated monomer (b), and the hydrophobic unsaturated monomer (b) comprises an alkyl (meth) acrylate having a hydrocarbon chain having 1 to 45 carbon atoms.

* * * * *